US012691002B2

(12) United States Patent
King et al.

(10) Patent No.: US 12,691,002 B2
(45) Date of Patent: Jul. 28, 2026

(54) CERVIX STABILIZING DEVICE

(71) Applicant: University of Cincinnati, Cincinnati, OH (US)

(72) Inventors: Anna King, Rocky River, OH (US); Lillian Orians, Wharton, OH (US); Rucha Tadwalkar, Mason, OH (US); Aaron Burdette, Sarasota, FL (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 19/075,225

(22) Filed: Mar. 10, 2025

(65) Prior Publication Data

US 2025/0281322 A1 Sep. 11, 2025

Related U.S. Application Data

(60) Provisional application No. 63/563,134, filed on Mar. 8, 2024.

(51) Int. Cl.
A61F 6/18 (2006.01)

(52) U.S. Cl.
CPC ...................................... A61F 6/18 (2013.01)

(58) Field of Classification Search
CPC .... A61F 6/00; A61F 6/06–18; A61B 1/00–32; A61B 10/02; A61B 10/04; A61M 25/01–0194; A61M 31/00; A61M 31/007; A61M 37/00–0069
See application file for complete search history.

(56) References Cited

U.S. PATENT DOCUMENTS

2014/0326249 A1* 11/2014 Cappiello ........... A61M 31/007
128/830
2021/0205541 A1* 7/2021 King ..................... A61M 31/00

OTHER PUBLICATIONS

"Suction Retractor Eases Access to the Cervix", HospiMedica International Staff, pp. 1-2, posted Feb. 10, 2025.

* cited by examiner

*Primary Examiner* — Michelle J Lee
(74) *Attorney, Agent, or Firm* — DINSMORE & SHOHL LLP

(57) ABSTRACT

A cervix stabilizing device includes a handle comprising a handle body and a compartment within the handle body. A plunger includes a stopper that forms a seal against an inner wall of the compartment. An actuation assembly is operatively connected to the plunger and extends outward from a sidewall of the handle body. The actuation assembly is configured to be actuated relative to the sidewall of the handle body to retract the stopper within the compartment to increase a volume in the compartment distal of the stopper, which is used to generate a negative pressure in the compartment with the cervix stabilizing device in use. A shaft is connected to a distal end of the handle body and having a lumen extending therethrough that is in communication with the compartment such that negative pressure is increased in the lumen due to the negative pressure in the compartment.

12 Claims, 10 Drawing Sheets

102

100

Uterus

Cervix

Vagina (a) IUD is inserted through tube into uterus (b) Tube is removed (c) IUD in place

84

10

86

10

CERVIX STABILIZING DEVICE

CROSS-REFERENCE

This application claims the benefit of and priority to U.S. Provisional Application Ser. No. 63/563,134, filed Mar. 8, 2024, titled "Cervix Stabilization Device," the details of which are incorporated herein by reference.

TECHNICAL FIELD

The present disclosure relates to devices to aid in an IUD insertion.

BACKGROUND

This section is intended to introduce the reader to various aspects of art that may be related to various aspects of the present disclosure, which are described and/or claimed below. This discussion is believed to be helpful in providing the reader with background information to facilitate a better understanding of various aspects of the present disclosure. Accordingly, it should be understood that these statements are to be read in this light, and not as admissions of prior art.

Many people in the United States use birth control as a preventative measure to avoid getting pregnant. A current study from the CDC shows approximately 65% of women, ages 15-49, are using a method of contraception. Among the 65% of women using a method of contraceptive, approximately 14% of women use an IUD. An IUD, or Intrauterine Device, is a small, plastic T-shaped device that is placed inside the uterus (a reproductive organ where a fetus develops) to prevent pregnancy. FIG. 1 is a schematic of an IUD 100 placed inside a uterus 102.

There are two main types of IUDs: hormonal and copper. The brands of hormonal IUD include Mirena, Kyleena, Liletta, and Skyla. The only copper IUD brand is the Paragard. Planned Parenthood states that the hormonal IUD works by thickening the mucus in the cervix (the lower, narrow end of the uterus that forms a canal between the uterus and vagina), which helps block the sperm (male reproductive cell) from entering through the cervix. The hormonal IUD can also stop eggs from leaving the ovaries (reproductive organ in which ova are produced), also known as ovulation, which means there is no egg for the sperm to fertilize. If there is no egg, then there is no chance of pregnancy. Copper is a natural spermicide, so the ParaGard IUD makes it difficult for sperm to get to the egg.

Many women choose to get an IUD over other forms of contraceptives provided because they are low-maintenance, long-term, and more effective than other forms of birth control such as natural cycle tracking, withdrawal, oral medication, patch, Depo-Provera injection, vaginal ring, diaphragm, female condom, male condom, cervical cap, spermicide, Nexplanon implant, and sterilization. Some patients may choose the copper IUD over the hormonal IUD and other listed forms of birth control because it does not contain hormones. Side effects from receiving an IUD may include mood swings, migraines, acne, breast changes, hormonal changes, appetite changes, blood clotting, bloating, nausea, weight fluctuation, vaginal irritation, vaginal bleeding, and hair growth changes. Hormonal birth control is also linked to an increased risk of breast cancer, depression, thrombosis, and other cardiovascular diseases.

Some patients experience anxiety about the anticipated pain of the IUD insertion procedure. The pain may feel like a small labor cramp to some women. Based on HealthLine, during the first 24 hours after insertion, nearly 60% of people who have not given birth may experience moderate to severe pain. Around 30% reported moderate to severe pain up to 3 days later. One week after insertion, about 20% continued to have moderate to severe pain.

To prepare for the procedure, the clinician may advise the patient to take over-the-counter pain relief medication such as ibuprofen or Naproxen. If the patient has never had a child or has only had a cesarean section, some physicians may recommend taking prescription misoprostol to soften the cervix. The physician may also advise the patient to schedule the procedure for the week of their menstruation, so that the patient's cervix is naturally dilated.

FIG. 2 is a schematic showing an IUD insertion procedure. During the procedure, the clinician inserts the speculum, a sterile duckbill-shaped device used to gain a visual of the cervix and vagina during pelvic exams. The clinician cleans the outer surface of the cervix and the surrounding area with antiseptic solution. It is uncommon for clinicians to use pain medication, but some may apply local anesthesia to the area (Lidocaine). If necessary, the clinician may use a cervical dilator to widen the opening of the cervix. After setting up for the procedure, a tenaculum is inserted into the vagina to grasp the outer surface of the cervix to stabilize and to move the cervix into a more ideal position for IUD insertion.

Once the cervix is stabilized, a physician inserts a device called a uterine sound to measure the length of the uterus by advancing it into the uterus until the fundus (the part of the uterus that is farthest from the opening; top part of uterus across from the cervix) is reached. They remove the sound and note the uterus' depth in the patient's records. A depth measurement of six to nine centimeters is expected. If it is under six cm, an IUD shall not be inserted into the patient's uterus. FIG. 3 is an image of instruments used for IUD insertion, including a Speculum 104, Sound 106, and Tenaculum 108.

After getting exact measurements of the uterus, the clinician will begin to assemble the IUD. For a copper IUD, this is done by opening the IUD packaging and placing the IUD into the introducer by folding the arms of the device down together and pushing it into the insertion tube. FIG. 4 is a schematic showing an IUD Introducer 110 in a uterus 112. For the hormonal IUDs the arms are bent upwards using the slider on the introducer which pulls the IUD inside the tube. If the threads of the IUD are external, the clinician secures them to the handle of the device using a cleft. The clinician then places the flange on the introducer to the measured depth of the patient's uterus. For a copper IUD, they insert the IUD to the full depth of the uterus. For the hormonal IUDs the introducer is inserted until the flange is about 2 cm away from the outer surface of the cervix. The clinician pauses for a few seconds to allow the arms of the IUD to open. They then push the insertion tube the rest of the way into the uterus until the flange on the tube is against the outer surface of the cervix, pushing the IUD to the fundus. They then release the IUD from the insertion device by either moving the slider on the handle or removing the insertion rod, then remove the insertion tube, leaving the IUD in the uterus. The tenaculum is removed from the cervix. The clinician then uses long suture scissors with a curved end to cut the threads of the IUD in the vaginal canal. The threads are cut to be approximately 3 cm from the cervix. The clinician then removes the speculum, concluding the procedure.

After the procedure, the clinician may provide feminine products like panty liners and pads in case the patient experiences vaginal spotting or bleeding. The patient puts their clothing back on and can leave the facility when they feel ready. After getting their IUD inserted, women may experience some minor cramping for the rest of the day. It is important for the patient to get some rest after this procedure and take medication if the pain worsens. If there is unusual bleeding or side effects that seem to worsen, the patient should call their clinician to determine if there is an underlying problem. IUD expulsion/misalignment is rare. The chance of these complications can increase up to 30% if you get an IUD placed after receiving an abortion or after labor. Some side effects of IUD misalignment are terrible cramping, unusual bleeding, fever, or any other unusual symptoms. It is important for the patient to communicate with their primary provider if any issues arise. FIG. 5 is a schematic showing a mispositioned IUD 114.

The main complaint about IUD insertion from patients is the high level of pain the procedure causes. Clinicians are not required to offer patients medications for pain. Most clinicians recommend that the patient takes Ibuprofen, an over-the-counter anti-inflammatory drug to treat mild pain, prior to their appointment. Some clinicians opt to give their patients Lidocaine-prilocaine cream which is applied to the cervix during the procedure as a local anesthetic as a pain prevention technique. This cream works to numb and soften the outside of the cervix which helps mitigate the pain caused by the tenaculum, but it does not reduce the pain associated with the insertion of the sound of IUD. Rarely, a paracervical block, which is a local anesthetic that blocks nerves and is delivered via injection, is used. This is seldom used due to the injection itself causing pain and the cost.

Physicians identify one of the main sources of pain as the tenaculum application to the cervix and insertion through the cervix. One way to reduce the pain to the cervix caused by the tenaculum is to use an alternative device, an Allis clamp that causes less trauma to the cervix because it does not pierce the tissue. The issue with this device is the shape of the cervix often prevents the physician from being able to get a sufficient hold on the cervix with the Allis clamp. A device in the market called Aspivix exists. It works by securing the cervix through suction rather than grasping. This device is expensive, which increases the cost of the procedure and is not as effective as the tenaculum in stabilizing the cervix. Therefore, a need still exists for an improved device to aid in an IUD insertion.

SUMMARY

In one embodiment, a cervix stabilizing device includes a handle comprising a handle body and a compartment within the handle body. A plunger includes a stopper that forms a seal against an inner wall of the compartment. An actuation assembly is operatively connected to the plunger and extends outward from a sidewall of the handle body. The actuation assembly is configured to be actuated relative to the sidewall of the handle body to retract the stopper within the compartment to increase a volume in the compartment distal of the stopper, which is used to generate a negative pressure in the compartment when the cervix stabilizing device is in use. A shaft is connected to a distal end of the handle body and having a lumen extending therethrough that is in communication with the compartment such that negative pressure is increased in the lumen due to the negative pressure in the compartment.

In another embodiment, a cervix stabilizing device includes a handle comprising a handle body and a compartment within the handle body. A plunger includes a stopper that forms a seal against an inner wall of the compartment. An actuation assembly is operatively connected to the plunger and extends outward from a sidewall of the handle body. The actuation assembly is configured to be actuated relative to the sidewall of the handle body to retract the stopper within the compartment to increase a volume in the compartment distal of the stopper, which is used to generate a negative pressure in the compartment with the cervix stabilizing device in use. A shaft is connected to a distal end of the handle body and having a lumen extending therethrough that is in communication with the compartment such that negative pressure is increased in the lumen due to the negative pressure in the compartment.

BRIEF DESCRIPTION OF THE DRAWINGS

The objects and advantages of the present disclosure will be further appreciated in light of the following detailed descriptions and drawings in which.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is a hand-held device that applies suction to the cervix to stabilize and position it during IUD insertion (referenced herein as the "Cervus Cervix Stabilizing Device"). It is used after the speculum is positioned and before/during the sound device and IUD introducer is used. The shaft and cervical interface of the device are inserted into the vaginal canal and held against the surface of the cervix. As the clinician activates the device, the device applies a suction force to the cervical tissue to grasp the cervix and hold it in place. This suction is applied while the sound is used to measure the uterus depth and the IUD introducer is used to insert the IUD into the uterus. After the IUD is inserted, the clinician releases the suction on the patient's cervix and removes the device.

Embodiments described herein are directed to the cervix stabilizing device that includes a handle that includes a handle body. The handle includes a compartment within the handle body and a plunger comprising a stopper that forms a seal against an inner wall of the compartment. An actuation assembly is operatively connected to the plunger and accessible from outside the handle body. The actuation assembly is configured to retract the stopper within the compartment to increase a volume distal of the plunger in the compartment and provide a negative pressure in the compartment with the cervix stabilizing device in use. A shaft is connected to a distal end of the handle body and has a lumen extending therethrough that is in communication with the compartment such that negative pressure is increased in the lumen due to the negative pressure in the compartment. The actuation assembly is arranged and configured to be manually actuated with the same hand holding the handle body.

Figure 1:
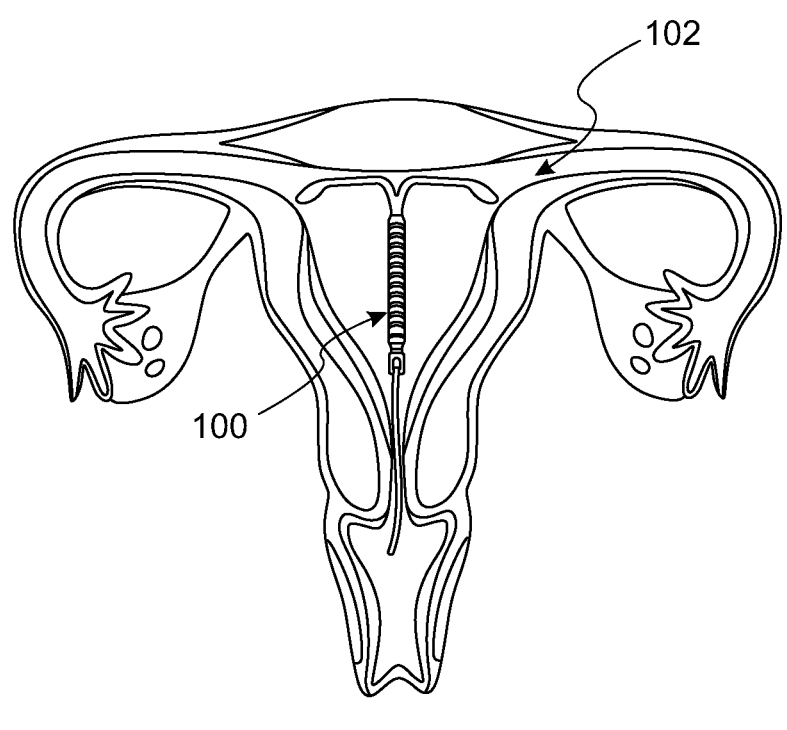
FIG. 1 is a schematic of an IUD placed inside a uterus.
Figure 2:
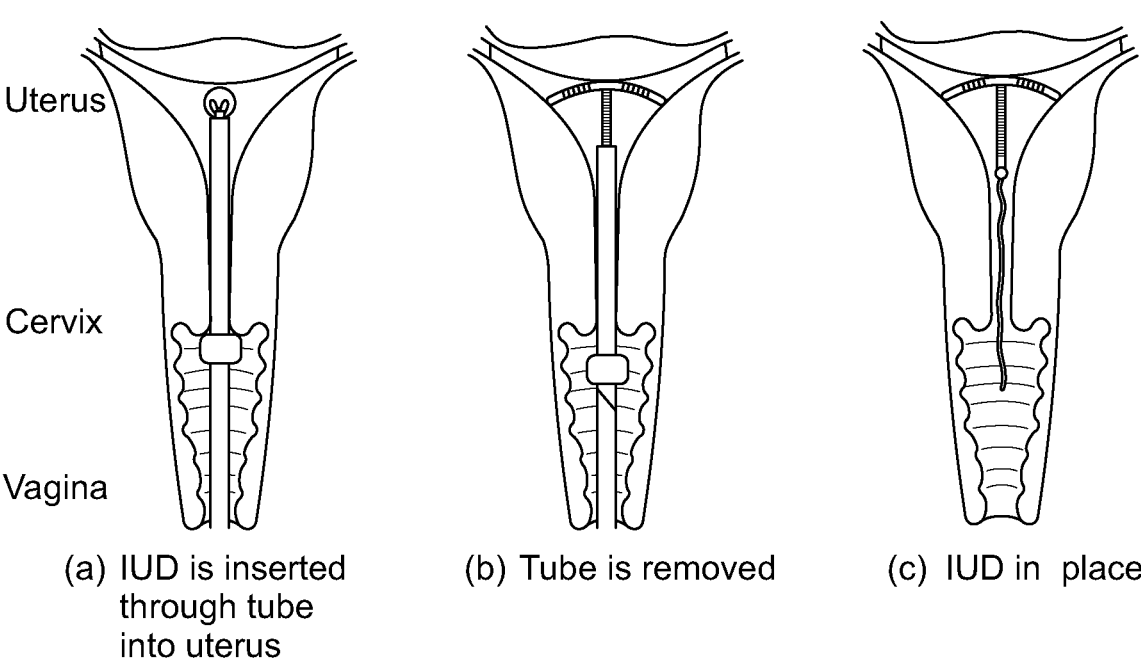
FIG. 2 is a schematic showing an IUD insertion procedure.
Figure 3:
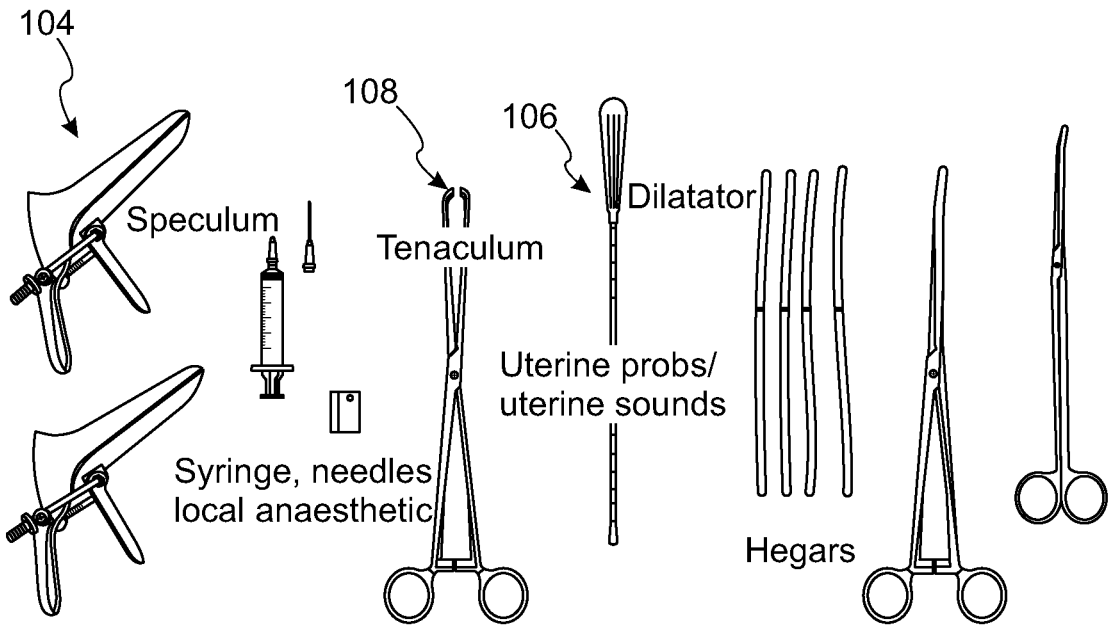
FIG. 3 is an image of instruments used for IUD insertion, including a Speculum, Sound, and Tenaculum.
Figure 4:
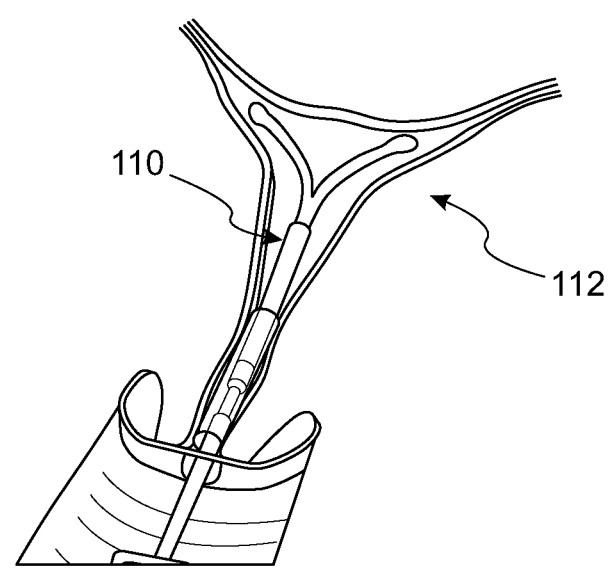
FIG. 4 is a schematic showing an IUD Introducer in a uterus.
Figure 5:
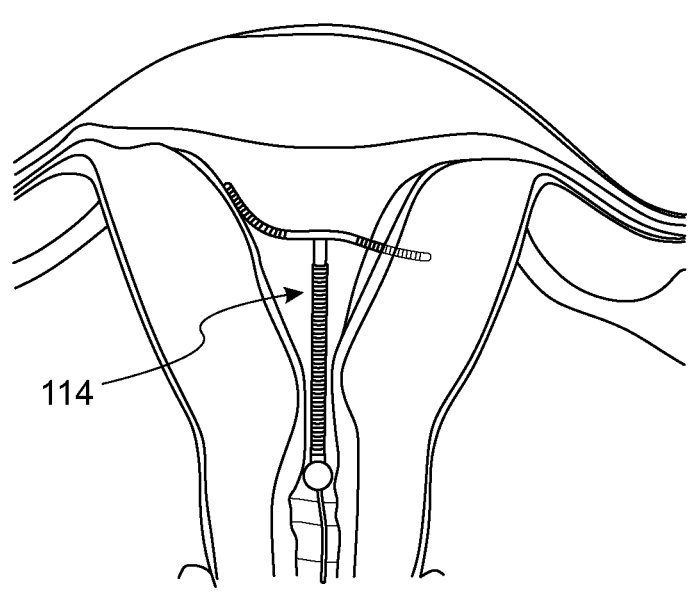
FIG. 5 is a schematic showing a mispositioned IUD.
Figure 6A:
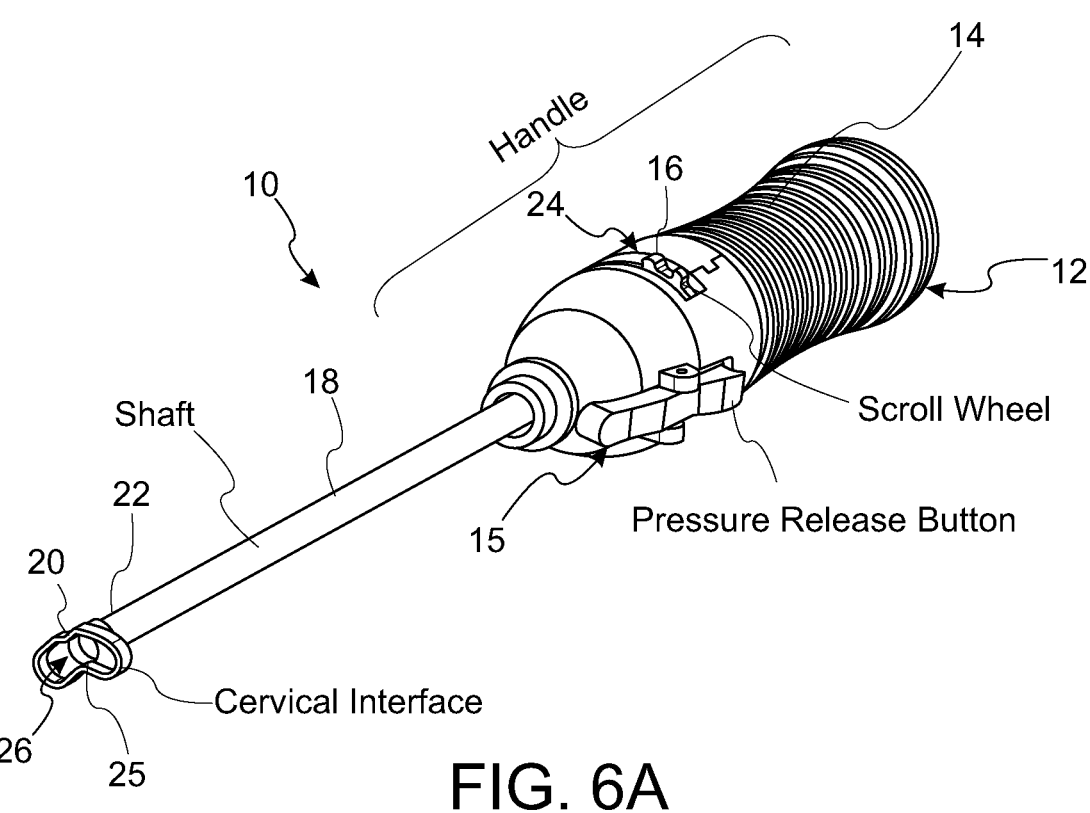
FIG. 6A is a schematic showing a perspective view of an embodiment of the device of the present disclosure.
Figure 6B:
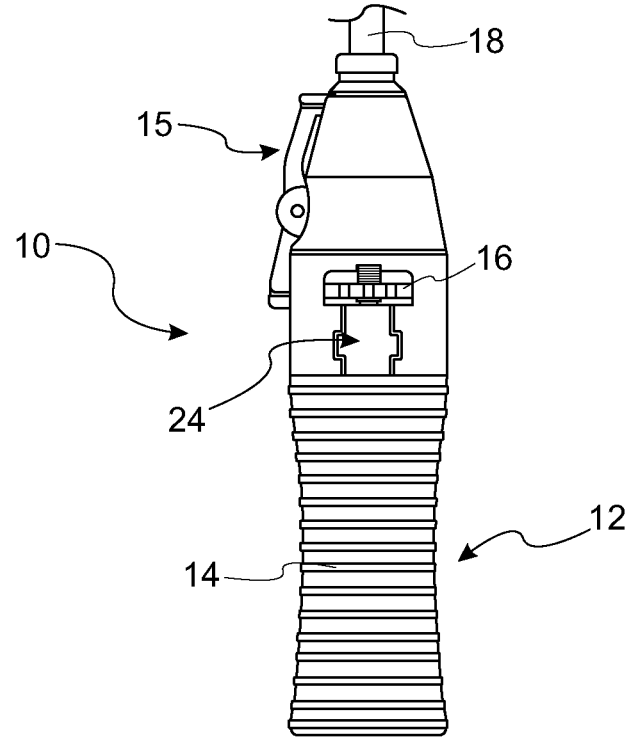
FIG. 6B is a schematic showing a side view of an embodiment of the device of the present disclosure.
Figure 6C:
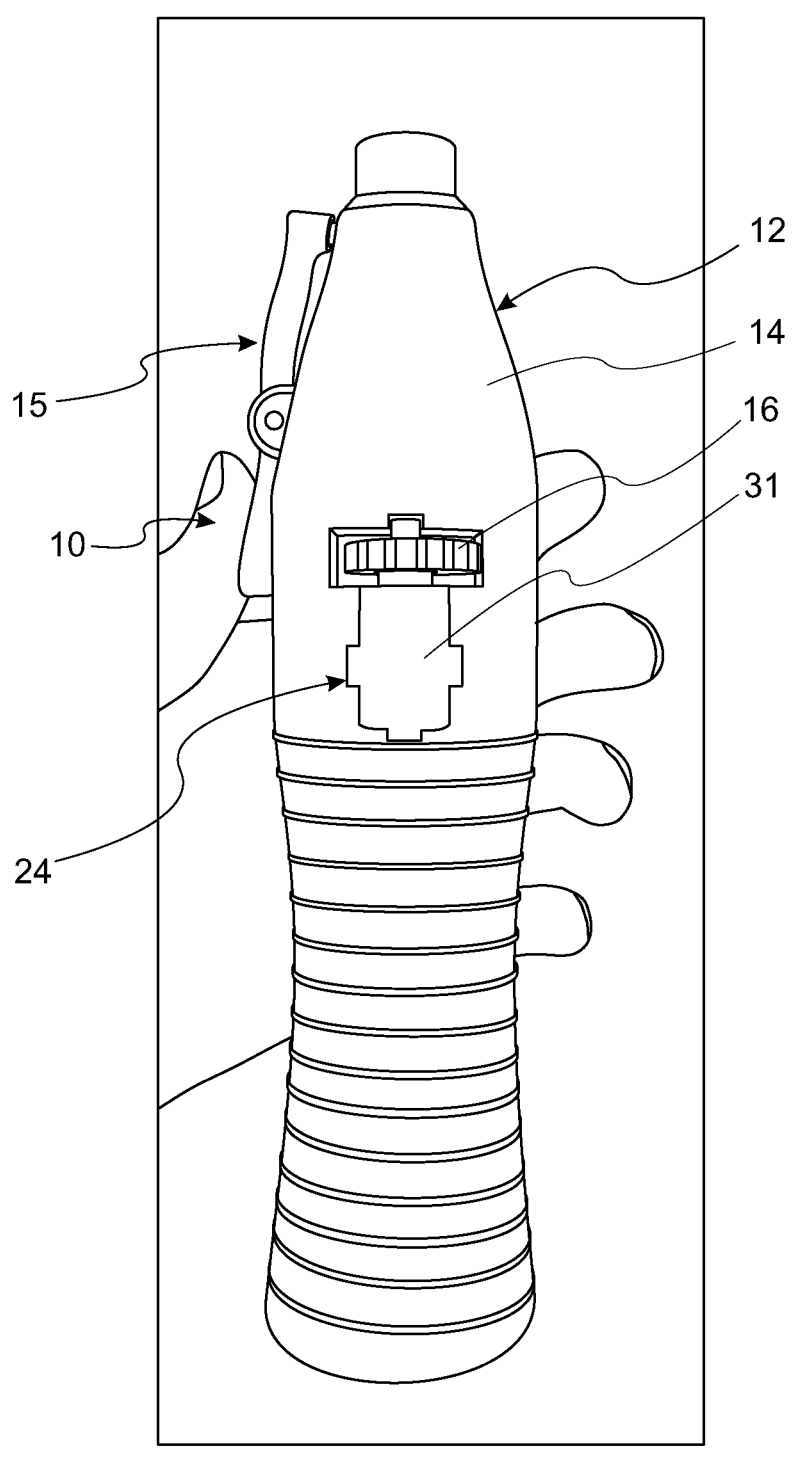
FIG. 6C is an image of an embodiment of the device of the present disclosure.

Referring to FIG. 6A, the device 10 of the present disclosure comprises the handle 12 including a handle body 14, a pressure release button 15, a scroll wheel 16, a shaft 18, a cervical interface 20 connected to a distal end 22 of the shaft 18 and an actuation assembly 24 including scroll wheel 16 that is used by a user to generate a negative pressure within the shaft 18 that is communicated through opening 25 to a suction pocket 26 formed in the cervical interface 20. Negative pressure is a relative term and refers to a pressure below atmospheric pressure. FIGS. 6B and 6C show additional views of the device 10.

Figure 7A:
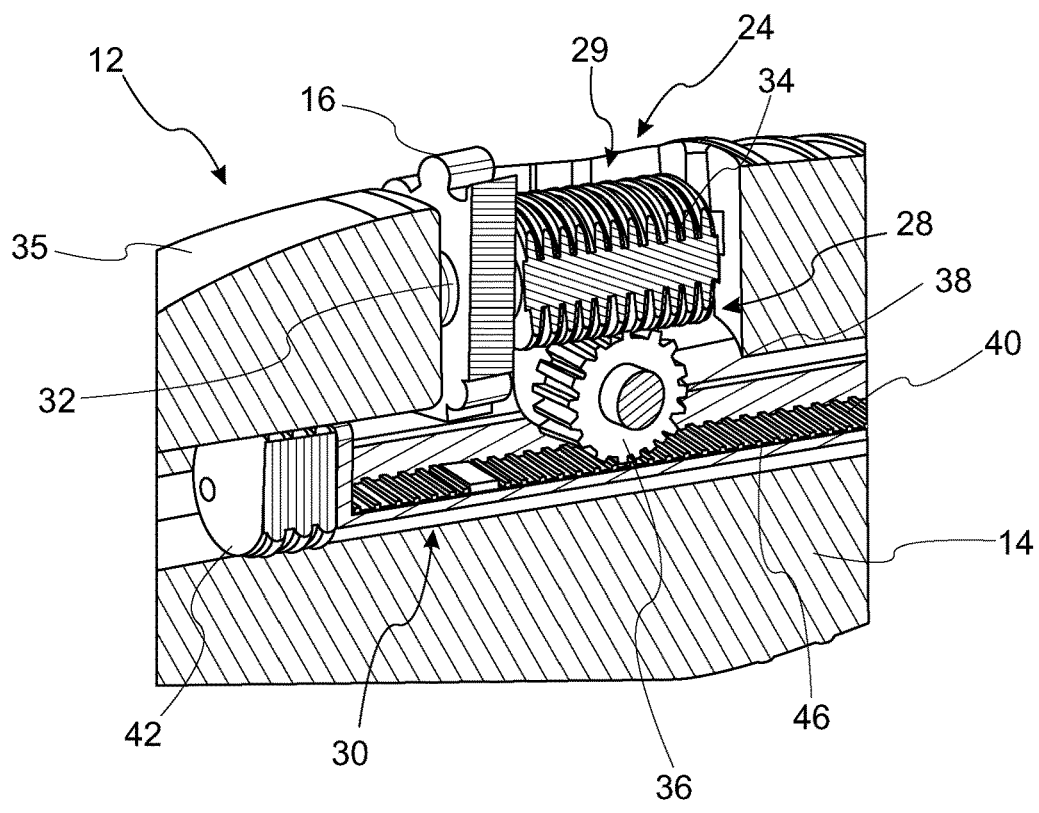
FIG. 7A is a schematic showing a section view of the device of the present disclosure showing the system of gears.
Figure 7B:
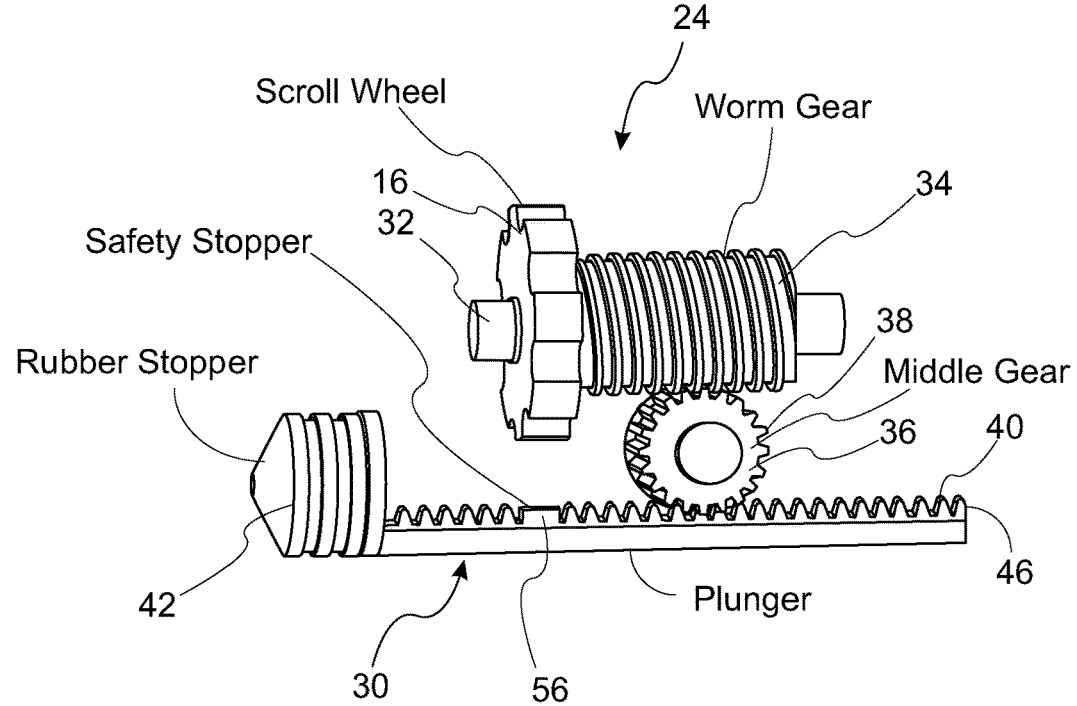
FIG. 7B is a schematic showing the gear system labeled.

Referring to FIGS. 7A and 7B, the handle 12 includes the actuation assembly 24 that includes a system of gears forming a gear train 28 that uses the force of the user spinning the scroll wheel 16 and mechanical advantage to pull back a plunger 30 to create negative pressure inside the handle body 14, shaft 18, and cervical interface 20 (FIG. 6A). As can be seen, the gear train 28 is placed in a compartment 29 that is recessed into the handle body 14, which can be covered by a door 31 (FIG. 6C). The scroll wheel 16 extends outward from a sidewall 35 of the handle body 14 and is on a same axle 32 as a worm gear 34 which causes the scroll wheel 16 and the worm gear 34 to spin in unison. As the worm gear 34 is turned by the user turning the scroll wheel 16 while holding the handle body 14 with the same hand for single-handed operation, the worm gear 34 interfaces with and turns a middle gear 36. As the middle gear 36 turns, teeth 38 of the middle gear 36 interface with teeth 40 of the plunger 30, pulling a stopper 42 proximally from a distal end 43 of the handle 12 (FIG. 8B) where the stopper 42 may interface with the handle body 14. In the illustrated example, the plunger 30 includes a rack or straight gear 46 having a row of side-by-side teeth 40 that are configured to engage the teeth 38 of the middle gear 36. The middle gear 36 is rotatably connected to the handle body 14, but does not translate relative to the handle body 14 such that rotation of the middle gear 36 causes the plunger 30 to translate between distal and proximal positions depending on the direction of rotation of the scroll wheel 16. In one embodiment, the gears may be made of stainless steel, for example, using a CNC machine. The gears 34 and 36 may be designed with larger teeth 38 and 40 that can provide more strength and reduce gear slippage due to a higher level of interaction between the teeth 34 and 36. The scroll wheel axle 32 may also be made of stainless steel, such as a rod that is cut to length.

Figures 8A, 8B:
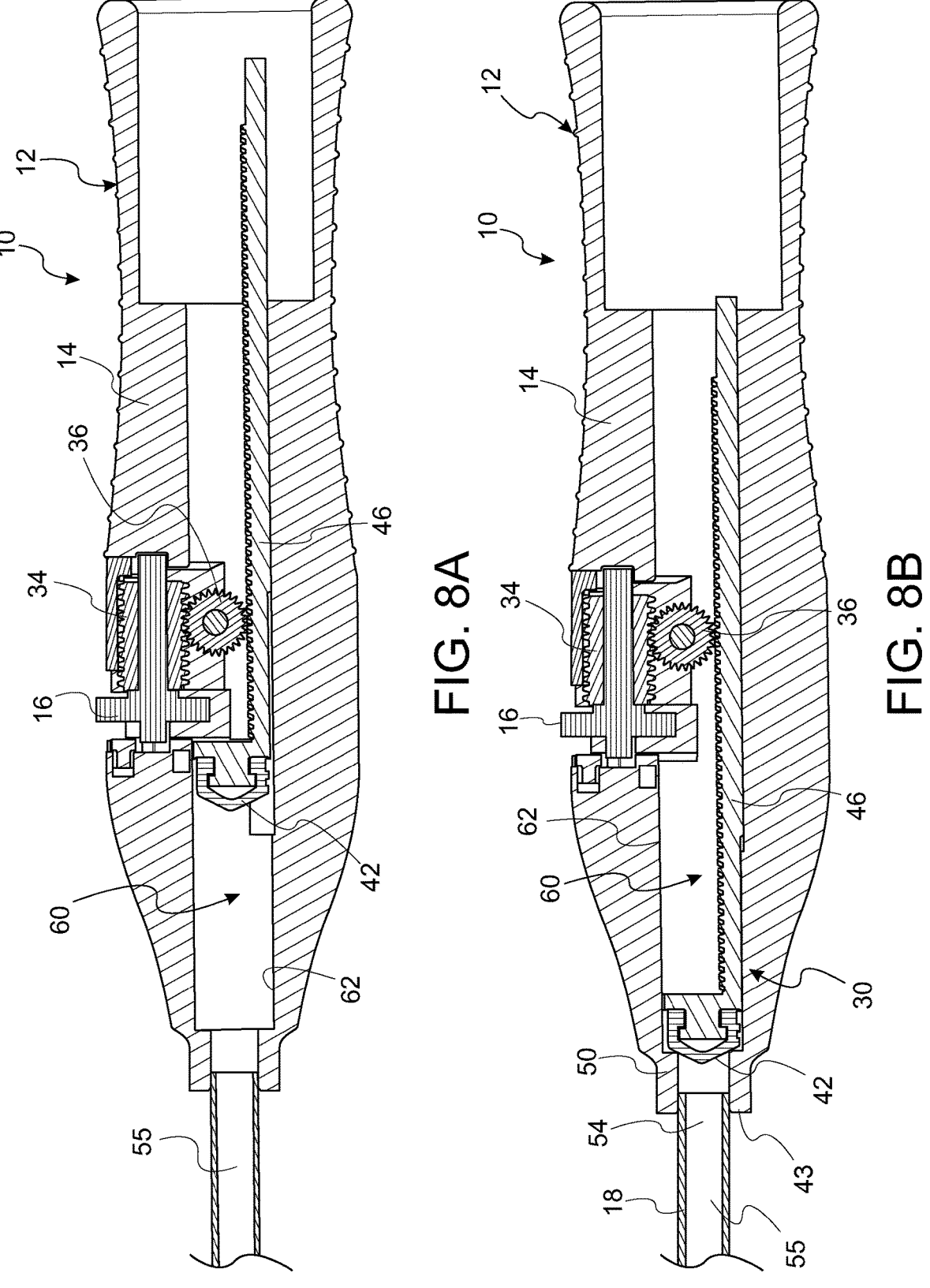
FIG. 8A is a schematic showing a partial section view of the device of the present disclosure in an initial configuration with a plunger fully extended.
FIG. 8B is a schematic showing the partial section of FIG. 8A with the plunger fully retracted.

FIG. 8A illustrates the plunger 30 in a distal position that is engaged with a necked-down, shaft connecting portion 50 of the handle body 14 that terminates at distal end 43 and is configured to slidably receive a proximal end 54 of the shaft 18, for example, in an interference fit. As discussed above, turning the scroll wheel 16 using one's thumb, engages the worm gear 34 to rotate, rotating the middle gear 36 counterclockwise in the example of FIG. 8A, which can cause the plunger 30 including the stopper 42 to move proximally to a proximal position, depending on the direction of rotation, illustrated in FIG. 8B thereby creating negative pressure when in use. Any suitable structures may be used to move the plunger 30, such as a ratchet arrangement. The negative pressure is then communicated to a lumen 55 that extends through the shaft 18 and then to the cervical interface 20 (FIG. 6A). Referring again to FIG. 7B, in some embodiments, the straight gear 46 may include a stop 56, which is configured to limit translation of the plunger 30, which also provides a limit on the negative pressure generated with chamber 60. Because the stopper 42 is sealingly engaged with an inner surface 62 of the chamber 60, moving the stopper 42 proximally increases a volume within the chamber 60 distal of the stopper 42, which can be used to generate suction at the cervical interface 20.

Figures 9A, 9B:
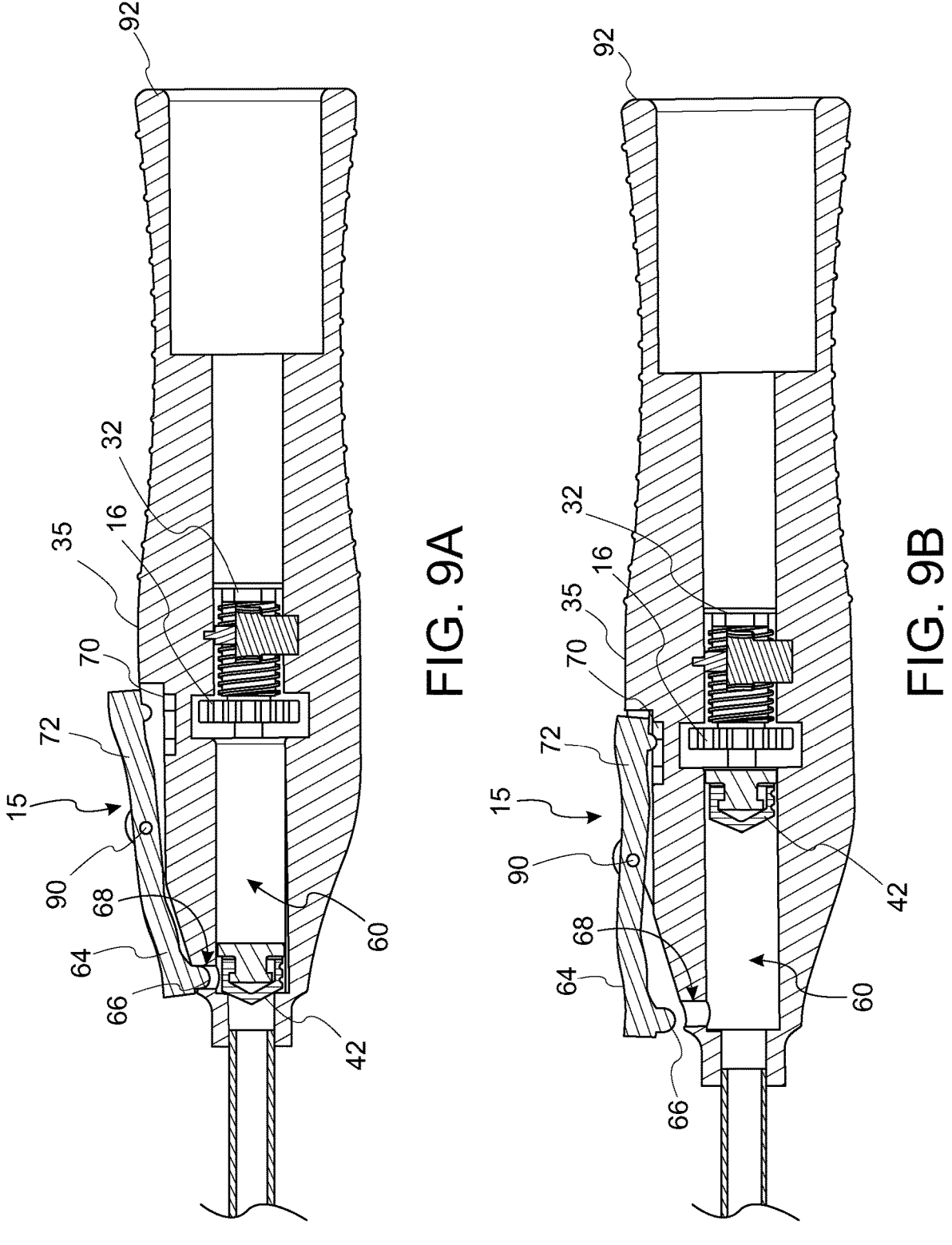
FIG. 9A is a schematic showing a partial section of the device of the present disclosure with a pressure release button in a closed position.
FIG. 9B is a schematic showing the partial section of FIG. 9A with the pressure release button in an open position.
Figure 10:
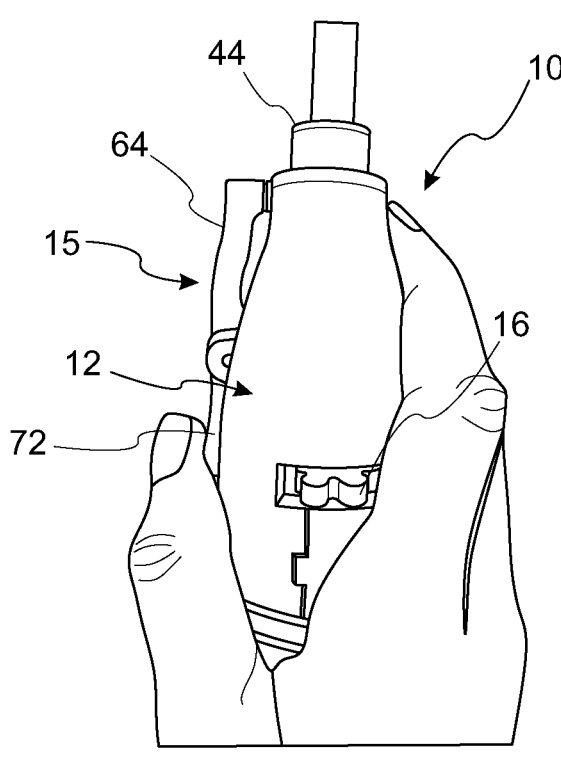
FIG. 10 is an image showing a user actuating the pressure release button of the present disclosure.

Referring to FIGS. 9A and 9B, the pressure release button 15 is pivotally mounted to the sidewall 35 angularly offset from the axle 32 and scroll wheel 16. In some embodiments, the offset angle may be about 90 degrees or less between the pressure release button 15 and the scroll wheel 16 to provide easy access to both the scroll wheel 16 and the pressure release button with the same hand that is holding the handle 12 to enable single-handed operation. In this regard, the position of the scroll wheel 16 may define a front of the handle 12 and the position of the pressure release button 15 may be at a side of the handle 12. In other embodiments, the offset angle between the pressure release button 15 And the scroll wheel 16 may be about 280 degrees or less. FIG. 9A illustrates the pressure release button 15 in a closed position with closing end 64 of the pressure release button 15 in a lowered position with a sealing protrusion 66 located in a hole 68 that extends through the sidewall 35 to the chamber 60. While the sealing protrusion 66 is illustrated as rounded, the sealing protrusion 66 may be any suitable shape such as more tapered, like a cone-shape, to facilitate gradual release of negative pressure from the chamber 60 to the surroundings. A resilient material 70 can be placed under a user end 72 of the pressure release button 15 to bias the pressure release button 15 toward the closed position. Any suitable device may be used to bias the pressure release button 15 toward the closed position, such as a spring. It should be noted that the negative pressure in the chamber 60 will also tend to bias the pressure release button 15 toward the closed position. When the user wishes to open the pressure release button 15, the user end 72 can be manually pressed with the same hand that is holding the handle 12 to release the pressure quickly as shown by FIG. 9B. If it is desired to release a small amount of pressure, the scroll wheel 16 can be rotated in an opposite direction with the pressure release button 15 in the closed position, which reduces the volume distal of the stopper 42. FIG. 10 shows the user manually opening the pressure release button 15 with a single hand.

Figure 11:
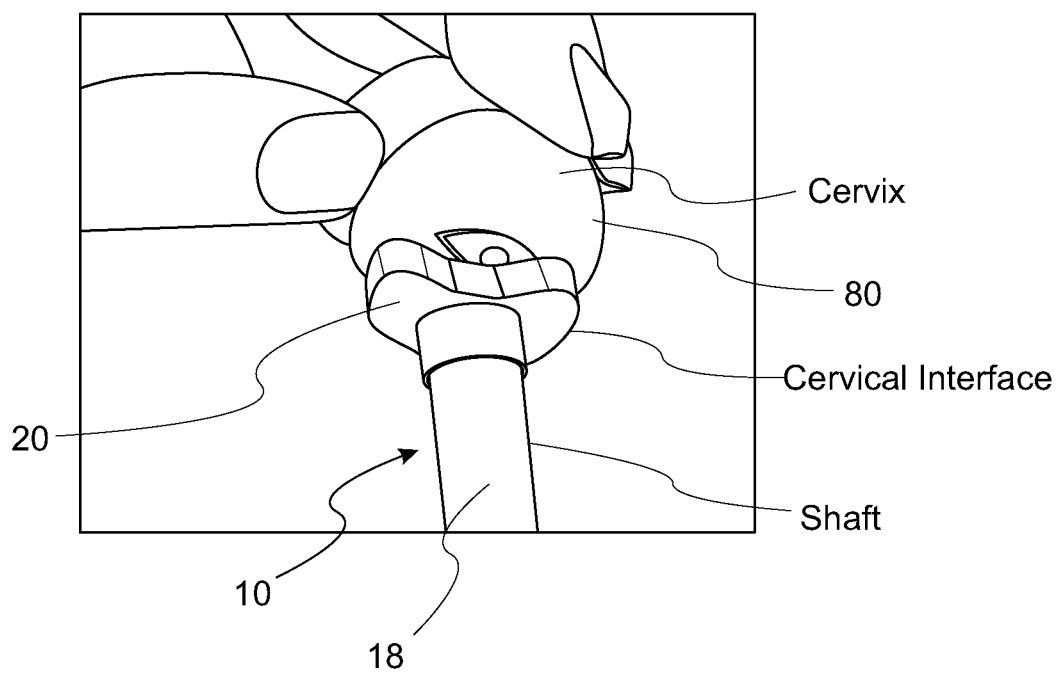
FIG. 11 is an image showing elements of an embodiment of the present disclosure, including the clear shaft and a cervical interface demonstration with an anatomical model of a cervix.
Figure 12A:
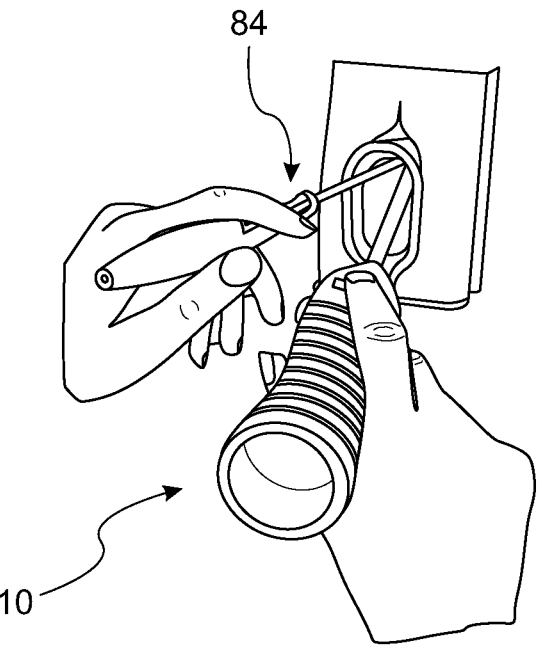
FIG. 12A is an image of an IUD Introducer in the left hand, and the device of the present disclosure in the right hand.
Figure 12B:
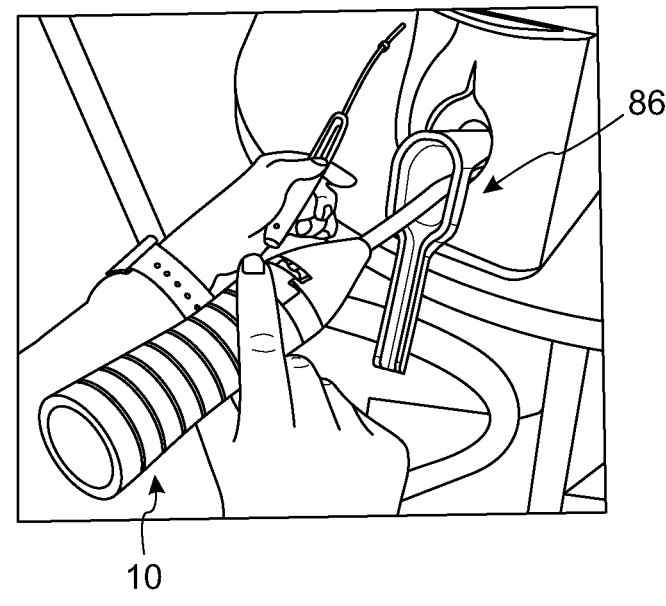
FIG. 12B is an image of an embodiment of the device of the present disclosure showing a demonstration with a speculum and an anatomical model of a vaginal canal and cervix.

Referring to FIGS. 11-12B, in use, a seal is created in use by the flexible cervical interface 20 against the cervical tissue 80, so while the plunger 30 is pulled, negative pressure is created in the handle 12, shaft 18, and cervical interface 20. That negative pressure suctions the cervical tissue 80 to grasp the cervical tissue. At maximum pressure, the device 10 may apply a little over 300 mmHg of negative pressure to the tissue 80, which is enough to counteract the force applied by the clinician inserting the IUD into the cervical canal herein referred to as stabilize, but not enough to cause trauma to the tissue. Once maximum suction is achieved, the user can remove their hand from the scroll wheel 16 since the mechanical advantage created by the gears 34 and 36 prevents them from moving backwards, thus locking the plunger 30 in place. If the clinician wishes to release some suction, they can turn the scroll wheel 16 in the opposite direction to move the plunger 30 back towards the top of the handle 12 (FIG. 8A). The plunger 30 may include the stop 56 on its gear teeth 40 to prevent the gears 34 and 36 from being able to pull it back further than the point where that maximum negative pressure is generated.

Referring also to FIGS. 9A and 9B, the pressure release button 15 located on the handle 12 is easy to activate while using the device that quickly releases the pressure in the chamber 60 of the handle 12. The pressure release button 15 may be a lever with the user end 72 extending from a pivot location 90 toward a proximal end 92 of the handle 12, near the user's hand and the other end 64 near the distal end 44 of the handle 12 (see FIG. 10). The user end 72 of the lever may be pushed up by a piece of silicone that acts like a spring or a spring may be used to keep the opposite end 64 of the lever down, maintaining a seal in the opening 68 that leads to the chamber 60 in the handle 12. When the user pushes the pressure release button 15, it compresses the silicone, lifting the opposite end of the pressure release button 15 out of the hole 68, allowing air to flow into the chamber 60, relieving the negative pressure inside of the chamber 60, releasing the force being applied on the cervical tissue 80. This pressure release button 15 can be used when the clinician is done with the procedure or needs to re-adjust the suction grip on the cervix.

Referring to FIG. 11, the shaft 18 is long enough to reach the cervix 80 through the vaginal canal and allow room for the IUD insertion device. In one embodiment, it is made of clear plastic material to allow visibility inside the vaginal canal during the procedure. The cervical interface 20 may also be made of clear, flexible silicone material to allow for visibility of the cervix and the ability to conform to the patient's anatomy. The cervical interface 20 may be shaped to match the curvature of the cervix. FIGS. 12A and 12B show an embodiment of the device 10 when used with an IUD Introducer 84 (FIG. 12A) or with a speculum 86 in an anatomical model of a vaginal canal and cervix (FIG. 12B).

The device 10 can be taken apart to fit inside of a standard autoclave machine for sterilization. The shaft 18 can be removed from the handle 12, and the cervical interface 20 can be removed from the shaft 18. The device 10 can be sterilized and reused or the device may be intended for a single use and be disposable.

Although not described in detail herein, other steps which are readily interpreted from or incorporated along with the disclosed embodiments shall be included as part of the disclosure. The embodiments that have been described herein provide specific examples to portray inventive elements, but will not necessarily cover all possible embodiments commonly known to those skilled in the art.

What is claimed is:

1. A method of using a cervix stabilizing device, the method comprising:
   holding a handle of the cervix stabilizing device in a single hand, the cervix stabilizing device comprising:
   the handle comprising a handle body, the handle comprising:
   a compartment within the handle body;
   a plunger comprising a stopper that forms a seal against an inner wall of the compartment; and
   an actuation assembly comprising a scroll wheel operatively connected to the plunger and extending outward from a sidewall of the handle body, the scroll wheel configured to be manually rotated relative to the sidewall of the handle body to retract the stopper within the compartment to increase a volume in the compartment distal of the stopper, which is used to generate a negative pressure in the compartment when the cervix stabilizing device is in use;
   wherein the scroll wheel and a worm gear are on an axle extending in a longitudinal direction of the plunger, and the worm gear is configured to drive a middle wheel directly engaged with a straight gear of the plunger to retract the stopper and generate the negative pressure; and
   a shaft connected to a distal end of the handle body and having a lumen extending therethrough that is in communication with the compartment such that negative pressure is increased in the lumen due to the negative pressure in the compartment; and
   a cervical interface on a distal end of the shaft configured to generate a seal against cervical tissue using the negative pressure in the lumen;
   placing the cervical interface on cervical tissue using the single hand;
   actuating the actuation assembly with the single hand with the cervical interface sealed against the cervical tissue thereby generating the negative pressure in the compartment.

2. The method of claim 1 further comprising releasing the negative pressure from the compartment using a pressure release button by actuating the pressure release button using the single hand.

3. The method of claim 2, wherein the pressure release button having a closed position configured to seal a hole through the sidewall that is in communication with the compartment and an open position that opens the hole through the sidewall.

4. The method of claim 3, wherein a position of the scroll wheel defines a front of the handle and the pressure release button is on a side of the handle.

5. The method of claim 2, wherein the pressure release button comprises a lever having a user end that extends from a pivot location of the pressure release button toward a proximal end of the handle.

6. The method of claim 1, further comprising rotating the scroll wheel with the single hand to retract the stopper.

7. The method of claim 1 further comprising disassembling the shaft from the handle body and the cervical interface from the shaft for a cleaning operation.

8. A cervix stabilizing device, comprising:

a handle comprising a handle body, the handle comprising:

a compartment within the handle body;

a plunger comprising a stopper that forms a seal against an inner wall of the compartment; and an actuation assembly comprising a scroll wheel operatively connected to the plunger and extending outward from a sidewall of the handle body, the scroll wheel configured to be manually rotated relative to the sidewall of the handle body to retract the stopper within the compartment to increase a volume in the compartment distal of the stopper, which is used to generate a negative pressure in the compartment when the cervix stabilizing device is in use; and wherein the scroll wheel and a worm gear are on an axle extending in a longitudinal direction of the plunger, and the worm gear is configured to drive a middle wheel directly engaged with a straight gear of the plunger to retract the stopper and generate the negative pressure; and a shaft connected to a distal end of the handle body and having a lumen extending therethrough that is in communication with the compartment such that negative pressure is increased in the lumen due to the negative pressure in the compartment.

9. The cervix stabilizing device of claim 8 further comprising a pressure release button having a closed position configured to seal a hole through the sidewall that is in communication with the compartment and an open position that opens the hole through the sidewall.

10. The cervix stabilizing device of claim 9, wherein a position of the scroll wheel defines a front of the handle and the pressure release button is on a side of the handle.

11. The cervix stabilizing device of claim 9, wherein the pressure release button comprises a lever having a user end that extends from a pivot location of the pressure release button toward a proximal end of the handle.

12. The cervix stabilizing device of claim 8 further comprising a stop carried by the straight gear that is configured to prevent movement of the plunger relative to the middle wheel in a proximal direction.

* * * * *